United States Patent [19]
Ritz et al.

[11] Patent Number: 6,062,075
[45] Date of Patent: May 16, 2000

[54] PROOF TESTING OF MECHANICAL HEART VALVES

[75] Inventors: Joseph P. Ritz, Austin; Axel D. Haubold, Liberty Hill; John L. Ely, Austin, all of Tex.

[73] Assignee: Medical Carbon Research Institute, LLC, Austin, Tex.

[21] Appl. No.: 09/224,816

[22] Filed: Dec. 30, 1998

[51] Int. Cl.$^7$ .............................. G01M 19/00; A61F 2/24
[52] U.S. Cl. ................................ 73/168; 73/1.72; 73/37; 623/2; 607/119
[58] Field of Search .............................. 73/1.72, 168, 37, 73/46, 49.4, 49.8, 865.6; 623/2, 3, 11, 12; 607/33, 119

[56] References Cited

U.S. PATENT DOCUMENTS

| | | | |
|---|---|---|---|
| 4,381,663 | 5/1983 | Swanson | 73/168 |
| 4,546,642 | 10/1985 | Swanson | 73/168 |
| 4,682,491 | 7/1987 | Pickard | 73/37 |
| 5,116,366 | 5/1992 | Hwang | 623/2 |
| 5,176,153 | 1/1993 | Eberhardt | 73/37 |
| 5,314,467 | 5/1994 | Shu | 623/2 |
| 5,487,760 | 1/1996 | Villafana | 623/2 |
| 5,531,094 | 7/1996 | More et al. | 73/168 |

OTHER PUBLICATIONS

Huffstutler, Jr., M.C., Ph.D., "Analytical Design Fundamentals of the Omniscience™ Cardiac–Valve Prosthesis", ASTM Symposium May 1981, pp. 1, 11–13.

Freiman, S.W., "Brittle Fracture Behavior of Ceramics", *Ceramic Bulletin*, vol. 67, pp. 392–402 (1988).

Quinn, G.D., "Strength and Proof Testing", *Engineered Materials Handbook*, vol. 4, pp. 585–598, ASM International (1991).

Ritchie, Robert O., "Fatigue and Fracture of Pyrolytic Carbon: A Damage–Tolerant approach to Structural Integrity and Life Prediction in 'Ceramic' Heart–valve Prostheses", *The Journal of Heart Valve Disease*, About 1998.

Transcript of FDA Panel Hearing concerning the Duromedics Bi–Leaflet Heart Valve (Feb. 7, 1986), pp. 1–81.

Primary Examiner—Helen C. Kwok
Attorney, Agent, or Firm—Fitch, Even, Tabin & Flannery

[57] ABSTRACT

A method and apparatus for proof testing an assembled mechanical heart valve prosthesis having a valve body and at least one movable occluder wherein at least one of the components has a surface of nonmetallic crystalline material, such as pyrocarbon, in which microcrack growth may occur. The assembled valve prosthesis is subjected to fluid loading with the occluder in the closed position so as to create omnidirectional pressure of at least 20 psig therewithin on the downstream side of the occluder. During fluid loading of the assembled valve, acoustic monitoring is carried out using a transducer to detect sounds that are indicative of crack nucleation and/or incremental crack extension, based upon a predetermined fail-pass criterion. Any valve prosthesis wherein sounds of a greater magnitude are detected is rejected.

20 Claims, 3 Drawing Sheets

PROOF TESTING OF MECHANICAL HEART VALVES

FIELD OF THE INVENTION

Background of the Invention

This invention relates to methods and apparatus for proof testing mechanical heart valves, and more particularly, to methods and apparatus for testing heart valves having one or more occluders which pivot and/or translate in moving alternately between open and closed positions, which valve includes at least one component of a material, such as pyrocarbon, in which microcrack growth may occur.

The replacement of human heart valves by skilled surgeons in the cardiovascular field has become relatively commonplace in the last two decades. Replacement valves of the mechanical type have become the valves of choice of many surgeons because their designs have generally been improved to such a degree that they have every expectation of remaining functional for the life of the recipient, inasmuch as they are not prone to potential problems of calcification that inherently trouble tissue valves which are designed to more closely mimic natural valves. Of these mechanical valves that have been developed, pyrocarbon has become the material of choice for both the tubular valve bodies and the occluders, as pyrocarbon has exhibited excellent strength and also resistance to degradation and thrombosis when exposed to body fluids. Pyrocarbon of a specific character, having a relatively high density of at least about 1.5 gm/cm$^3$, having an apparent crystallite size of about 200 Å or less and having high isotrophy was the first type of pyrocarbon that was found to exhibit remarkedly good properties for use in heart valves or the like and was used to coat substrates of graphite or the like having the approximate shape of the desired component.

Commercial versions of such pyrocarbon coatings commonly included carbide-forming alloying agents, usually silicon, to assure that the resultant pyrocarbon would have adequate structural strength, and up to about 20 weight % of silicon in the form of silicon carbide was felt to desirably be present in biomedical pyrocarbons so as to provide hardness and wear resistance needed to assure a long lifetime. Frequently, silicon in an amount of at least about 5 atom percent, based upon total atoms of carbon plus silicon, was present in pyrocarbon used in commercial heart valves, and typically such heart valve components were made from pyrocarbon containing between about 5 and about 12 weight % of silicon.

A number of commercial heart valves have been produced in the United States incorporating one or more components using such pyrocarbon coatings. Such components were first and still are commercially produced and marketed by Carbomedics, Inc. of Austin, Tex., as Pyrolite pyrocarbon. Such valves include the St. Jude Medical, Inc. valve, the Duromedics valve, which is illustrated in U.S. Pat. No. 4,443,894 and which was pioneered by Dr. Jerome J. Klawitter, and a mechanical heart valve and designed and marketed by Carbomedics, Inc.

More recently, a method was discovered for producing pyrocarbon without the inclusion of any alloying agent that has structural properties equal to or superior to those of the traditional silicon-alloyed pyrocarbons. Such processes and the resultant pyrocarbons are disclosed in U.S. Pat. No. 5,677,061. Graphite substrates coated with these pure pyrocarbons are commercially available, as On-X carbon, from the assignee of the present application, and this improved pyrocarbon is being used in commercial heart valves of the type shown in U.S. Pat. No. 5,641,324.

As a part of obtaining FDA approval in the United States to market certain of the above-mentioned prosthetic heart valves, such valves having pyrocarbon components were routinely subjected to proof testing. The Duromedics bileaflet mechanical cardiac valve prosthesis, that was developed in Austin, Tex. by Dr. Klawitter on behalf of Hemex Scientific, Inc. was assembled from pyrocarbon components produced by Carbomedics, Inc. and was proof tested using methods developed by Dr. Klawitter. Hydrostatic testing of the assembled valves was carried out using a pressure up to about 30 psig. Water was used for the hydrostatic testing and was applied to the assembled valve using a diaphragm. The exterior of the valve housing was not constrained so as to allow it to deform with pressure; thus, the procedure served as a test for both potential leaflet escape and leaflet and valve body fracture. Examination was carried out visually and by mechanical strain gauges to assure that no unusual stresses were induced during testing.

Subsequently filed U.S. Pat. No. 5,531,094 disclosed an apparatus for proof testing mechanical heart valves. During the proof test, a working fluid was supplied by a piston pump so as to cause the valve to close, and sufficient fluid pressure was then applied to exceed the calculated pressure necessary to provide an energy fracture of the leaflets. Generally, a working pressure of about 22 to 23 psig was used. Following successfully passing the proof test, the heart valve was subjected to a function test where a pulsatile flow of liquid through the valve was carried out.

U.S. Pat. No. 4,682,491 discloses a method and apparatus for testing prosthetic valves using a circulatory system which mimics the human circulatory system. The heart valve is tested in a manner in which it can be visually observed for suitability prior to implantation.

The inherent nature of all pyrolytic carbons and other such polycrystalline materials renders them potentially prone to the possibility of failure as a result of fatigue crack growth. Unfortunately, fatigue cracks grow intermittently as microcracks, and thus they might not be detected by a proof test which is dependent upon hydraulic loading to a value sufficient to provide a selected energy of fracture. Accordingly, a decision was made that other methods of proof testing should be pursued in order to improve the reliability of such pyrocarbon heart valve components.

SUMMARY OF THE INVENTION

It has now been discovered that assembled mechanical heart valves using components made of a material in which microcrack growth may occur and may potentially lead to failure, e.g. pyrocarbon components or components having pyrolytic carbon coatings upon graphite substrates, can be reliably proof tested by acoustic emission detection during fluid loading. A mechanical heart valve having at least one occluder set in the closed position is subjected to loading in its downstream region to a level that exceeds normal service loading but is less than a loading at which fracture would normally occur. Although point loading may be employed, omnidirectional fluid loading is preferably applied to the outflow surface of the occluder and the interior of the valve body, more preferably using a bladder. A pressure of at least about 10 psig is applied, and preferably at least 20 psig and more preferably at least about 25 psig is applied in order to represent conditions that would be substantially more severe than those encountered within the human body. Loading of such magnitude that is in excess of normal service loading is considered to be sufficiently high to cause crack nucleation, i.e. initiation, and/or incremental crack extension, i.e. propagation, to occur in pyrocarbon if inherent defects are present in such a component. Validation of this proof testing method has been carried out by showing that if such a component contains microcracks or defects that will lead to crack nucleation, audible emissions above a certain level can be detected during such loading. Thus, by appropriately monitoring the broad frequency range of about 10 kiloHertz (kHz) to about 1 megaHertz (mHz) for such emissions, the occurrence of either crack initiation or crack propagation in the material in question, e.g. pyrocarbon will be detected and will result in a rejection of the valve prothesis being tested.

This proof test method is unique in incorporating mechanical load and stress application upon an assembled mechanical heart valve while monitoring for acoustic emissions indicative of microcrack initiation or propagation. Although mechanical load application was previously used show structural integrity, the incorporation of the acoustic emission aspect of the test has now been found to enhance the overall resolution of such a proof test. The result is a provision of further assurance that performance of the test itself does not so strain the valve under test as to then render it more susceptible to ultimate fatigue crack propagation.

There is also provided apparatus for carrying out such proof testing of assembled mechanical heart valves having at least one movable occluder, e.g. the bileaflet heart valves that have become the mechanical valves of choice in the United States in the 1990's. The apparatus includes a fixture for supporting the valve with the occluder(s) in the closed position and preferably has a flexible bladder which can be positioned in association with the interior of the downstream or outflow region of the valve. The apparatus provides an arrangement for slowly filling the bladder with a suitable fluid, e.g. air, in order to apply omnidirectional pressure against the occluder(s) and the interior surface of the downstream section of the valve body. Positioned in contact with the exterior surface of the valve body are one or more acoustic sensors, which may include transducers in association with waveguides. The waveguides facilitate contact against the exterior surface of valves of different sizes and assure that any sounds emanating from the valve body or from an occluder therewithin will reach the associated transducer.

The preferred apparatus embodies a pressure chamber subassembly which includes the flexible bladder that, when pressurized, will extend into and fill the interior of the downstream end of the valve body, thereby applying omni-directional pressure to all of the surfaces therewithin. Once the assembled valve has been loaded in the test apparatus and latched in place, with the waveguides in contact with the valve body surface and with the transducers attached to electrical readout equipment, testing is carried out in a programmed manner. Assuming the valve passes the test, it is sent to final production and packaging.

DETAILED DESCRIPTION OF THE PREFERRED EMBODIMENTS

Very briefly, there is shown in the accompanying drawings a proof testing apparatus 11 which uses air to inflate a bladder which loads an assembled mechanical heart valve to a level that would cause no physical damage to unflawed components, but which shall cause a flawed component to initiate microcracking or cause an existing microcrack to propagate when critical stress levels are reached or exceeded. The apparatus 11 can be effectively used to proof test any assembled heart valve which has a component, either a valve body or an occluder, made of a material in which microcrack growth may develop that may potentially lead to failure following implantation into a human. The apparatus 11 employs an acoustic emission detection system (AEDS) 13 which will detect sounds emitted during the fluid loading of the assembled heart valve that are representative of the initiation or propagation of microcracks or other flaws. While an omnidirectional pressure of at least about 20 psig, and preferably about 25 psig, is applied to the interior of the downstream end of the valve, the system monitors, i.e. listens, for the emission of sounds that are representative of the initiation or propagation of microcracks in the assembled mechanical heart valve. A transducer is used which will convert those acoustic emissions to voltage signals that are read and/or recorded.

Figure 1:
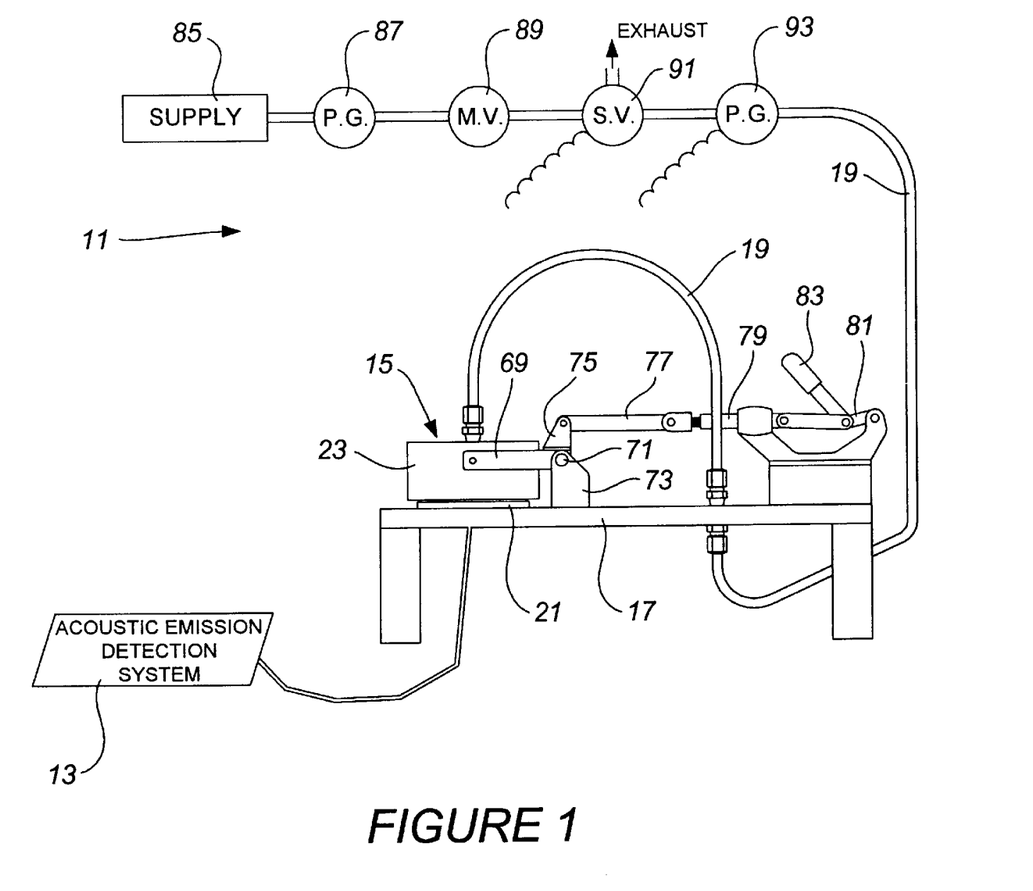
FIG. 1 is a diagrammatic view of apparatus for carrying out a proof testing method embodying various features of the invention, with the exception of a control system.
Figure 3:
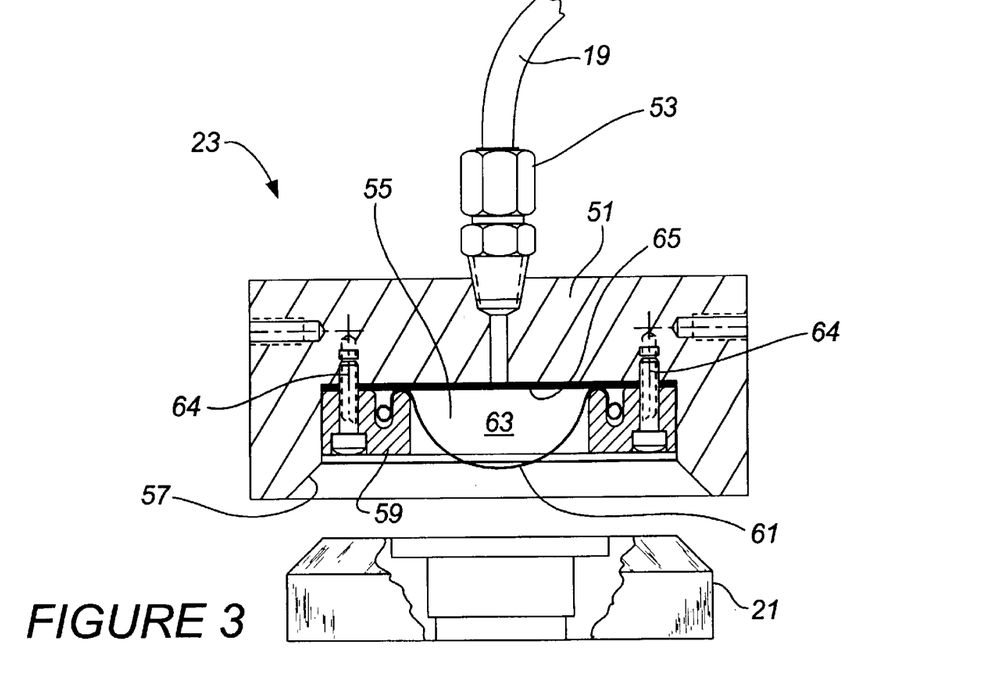
FIG. 3 is an enlarged view, primarily in section, showing features of the upper portion of the testing fixture illustrated in FIG. 1 and schematically showing the lower holder.
Figure 4:
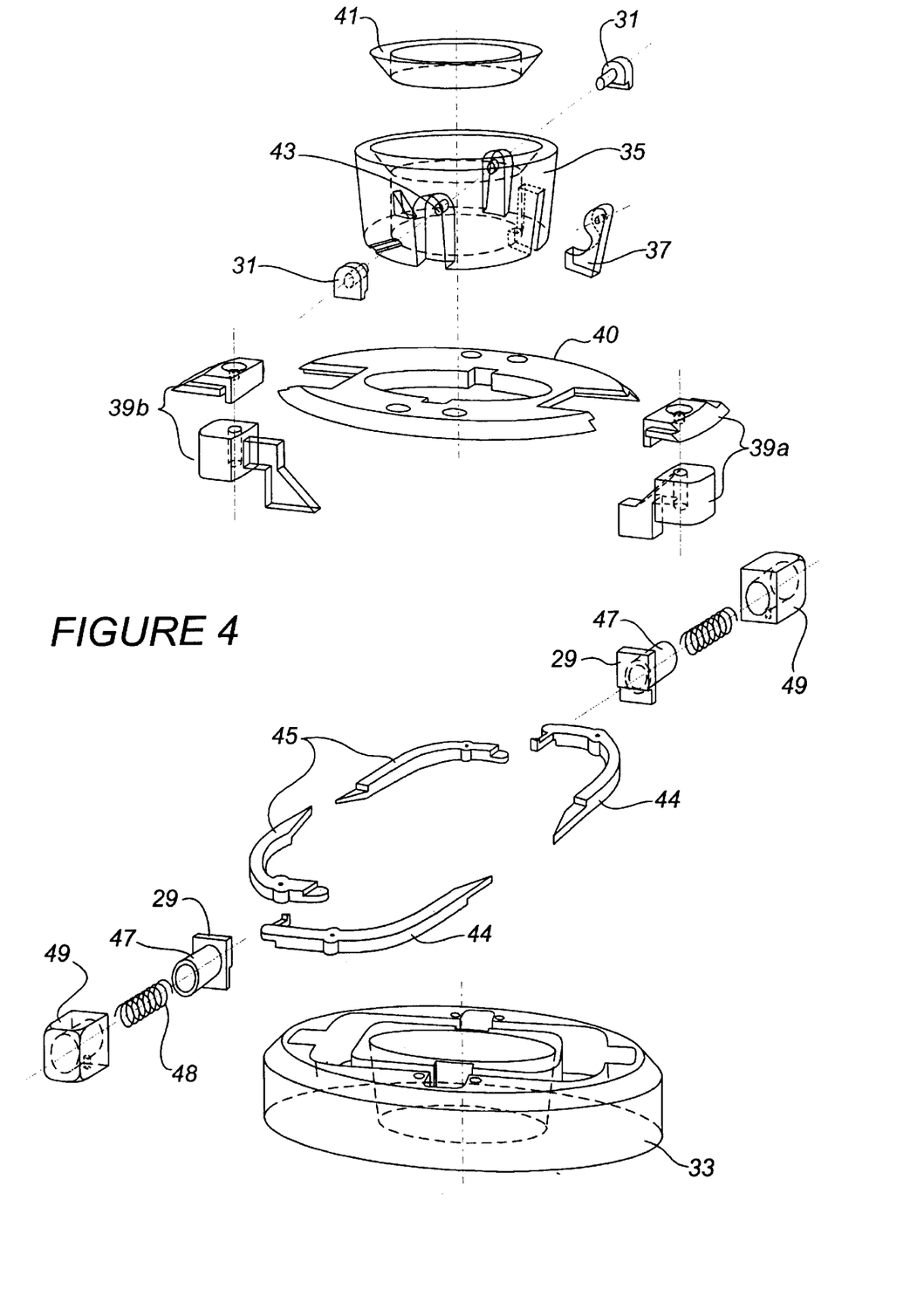
FIG. 4 is an enlarged exploded perspective view showing some details of the lower holder portion of the fixture for holding the valve being tested, illustrating the lifter or ejector for removing the valve from the fixture and the levers associated with the spring-loaded slides which carry the sensors and assure that physical contact is maintained between the waveguides and the exterior surface of the valve body.

The proof testing apparatus 11 that is illustrated in FIG. 1 which includes a holding fixture assembly 15 mounted on an appropriate stand 17. The assembly is connected through conduit means 19 to a source of fluid pressure and electrically connected to the acoustic emission detection system (AEDS) 13. The holding fixture 15 is designed to accommodate mechanical valves of different sizes. It is more particularly illustrated in FIGS. 3 and 4 of the drawings, which show that it includes a lower holder section 21 and an upper cap section 23. The valve to be proof tested is carefully placed in the holder section 21 with its occluders in the closed position, where they will stay as a result of gravity. Then the cap section 23 is closed and latched using a toggle mechanism 81 that is mounted on the stand 17, and the proof test is ready to begin.

Figure 2:
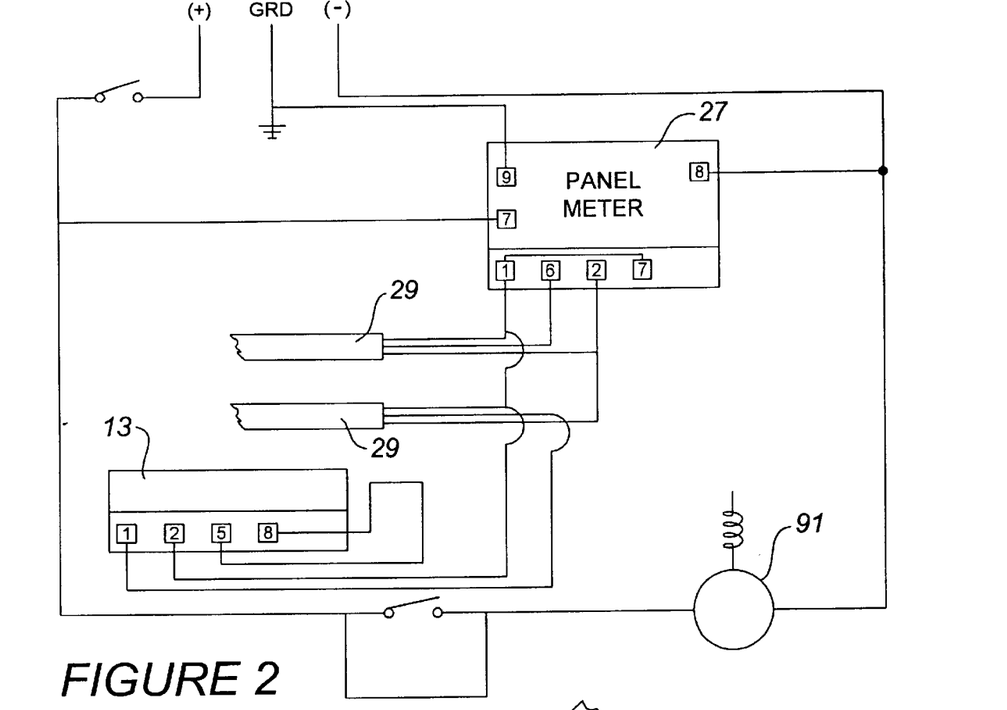
FIG. 2 is an overall schematic view of a control system for use with the apparatus of FIG. 1.

The AEDS 13 associated with the holding fixture is depicted in the schematic that is included as FIG. 2. In the arrangement illustrated, two sensors are utilized which each employ a pressure transducer 29 and an associated waveguide 31. The two pressure transducers are suitably electrically connected to voltage meters in the panel 27 to provide a visual indication and to the AEDS 13 which analyzes and records the voltage signals. Fluid loading of the interior portion of the downstream end of the mechanical valve is carried out by pneumatically pressurizing a bladder that is included in the cap section of the holding fixture. During such fluid loading of the downstream portion of the valve with the occluder in the closed position, significant flaws in a component made of pyrocarbon or the like are detected by monitoring for acoustic emissions.

More specifically, the proof testing apparatus 11 is designed to carry out quality control testing on tubular heart valves where the components of the valve, i.e. a tubular valve body and at least one occluder, are in assembled condition. Such mechanical valves may have only a single occluder or may have multiple occluders, for example having two, three or more leaflets. The mechanical heart valves of choice in the United States today are bileaflet valves having two occluders, and for purposes of explanation, reference is sometimes hereinafter made to the On-X bileaflet valve shown in U.S. Pat. No. 5,641,324. It employs a pair of leaflets of generally semicircular shape that independently translate and then pivot along two parallel axes to essentially completely close the blood flow passageway through the tubular valve body when in the closed position. By "assembled", it is meant that the occluder or occluders are operatively mounted so that they will function so as to move or swing between the open and closed positions. The lower holder section 21 of the fixture 15 is designed to receive the valve with its downstream end pointing upward so that gravity will urge the leaflets to remain in the closed position. Although testing in such an orientation is convenient and efficient, it should be understood that testing may be carried out in other orientations.

As previously indicated, the proof testing apparatus 11 is designed to be employed for quality control of mechanical heart valves wherein one of the components is made from a structural material in which the growth of microcracks may occur, particularly crystalline nonmetallic materials. One such material of particular interest is pyrolytic carbon, i.e. pyrocarbon. Prosthetic heart valve components can be made entirely of pyrocarbon, but more usually they will be made from isotropic graphite that is coated with pyrocarbon so that the exterior surface of the component is completely pyrocarbon, i.e. the substrate is totally enveloped during the manufacturing process when the pyrocarbon is deposited from a vapor atmosphere. Accordingly, when the terminology pyrocarbon is used as a part of this application, it should be understood that it covers both components made of substantially all pyrocarbon and those having substrates of graphite or the like that are coated with pyrocarbon upon their exterior surfaces.

Valves are preferably proof tested prior to the installation of the surrounding sewing ring that allows the complete heart valve assembly to be sutured in place in the heart of the recipient. Not only might the presence of the suture ring interfere with establishing coupling between the sensor and the exterior surface of the assembled valve (the acoustic emission detection arrangement that is employed in the illustrated embodiment), but it is also more economical because the cost of installation of a sewing ring onto a valve body is incurred only after proof testing when it has been ascertained that the valve will meet all quality control standards.

As previously indicated, the holding fixture 15 includes a bottom holder section 21 and an upper cap section 23, and the tubular valve is first placed in the holder section before the cap section 23 is closed in place. The holder section 21 includes a main body 33 which is appropriately affixed to the stand 17 by cap screws or the like, and it is designed to accommodate a replaceable cup or receiver 35 centrally therewithin. The cup 35 includes a pivoting lifter 37 for axially raising the valve above the upper edge of the cup to facilitate removing the heart valve therefrom following testing, and the main body 33 of the fixture includes two thumb-operated, slidable ejectors 39. The right-hand ejector 39a (FIG. 4) withdraws the transducers 29 by pivoting a pair of levers 44 which directly engage the waveguides 31, and, as a part of its final movement, the ejector 39a actuates the lifter 37. The opposite slidable ejector 39b pivots the levers 45 to withdraw spring-loaded slides 47 which engage the waveguides 31, thereby freeing the cup 35 and allowing the cup and its associated pair of waveguides 31 to be removed and replaced with a cup designed to hold a heart valve of a different size or of a slightly different design. Final movement of the actuator 39b cams the cup 35 upward in the main body 33 and assists in its removal. The slides 47 have a cylindrical shape and carry compression springs 48, both of which are received in cavities formed in short housings 49 that are received in the main body 33 of the fixture. A cover plate 40 is mounted atop the main body 33 of the holder and secures the components in their assembled condition.

The cup 35, when installed in the lower holder 21 of the fixture is designed to receive the valve with its downstream end pointing upward. The inlet end of the On-X valve has a toroidal surface which constitutes the largest diameter portion of the valve body, and it is accommodated at the bottom of the cup 35. The downstream end of the valve body is centered through the use of an adaptor ring 41 having a central circular opening that fits closely about the outer cylindrical surface of the downstream section of the heart valve and a frustoconical outer edge surface that mates with the upper interior edge of the cup, thereby filling the region of the cup outside the downstream end of the valve. The cup 35 has a pair of diametrically opposed passageways 43 of circular cross-section which accommodate the end portions of the diametrically opposed waveguides 31 that slide inward and outward in the passageways in order to make contact with the exterior surface of the pyrocarbon valve body that is installed in the cup. When the cup 35 is being placed in the main body of the holder, the thumb actuator 39b is used to pivot the first pair of curved levers 45 so as to withdraw the pair of spring-loaded slides 47 that engage the radially outer ends of the waveguides 31, normally biasing them inward into physical contact with the valve body. The radially outer ends of the waveguides 31 are in physical contact with the transducers 29 which are carried by the slides and which are preferably piezoelectric elements. Preferably, piezoelectric crystals are employed which produce a voltage when an acoustical signal is received, and these voltage signals are transmitted through conductors to the AEDS 13.

The cap portion 23 of the holding fixture 15 includes a housing 51 that is closed at its upper surface except for a central passageway which connects via a suitable fitting 53 to the line 19 through which fluid under pressure is supplied. The housing 51 has a downwardly open central chamber 55 formed therein, and a frustoconical edge region 57 of the undersurface of the housing 51 constitutes the periphery of the chamber 55 and is shaped to mate with the upper surface of the holder section 21. An annular retainer 59 is received within the chamber 55 and secures an expandible resilient bladder 61 (made of any suitable elastic material) that provides an essentially closed pressure chamber 63. The bladder 61 serves as the movable wall of the pressure chamber which is caused to expand in response to the application of fluid pressure through the supply line 19 and contract in response to the withdrawal of fluid therefrom by exhausting the chamber to the atmosphere. In the illustrated embodiment, the retainer 59 is mounted by a plurality of socket screws 64, and a suitable resilient gasket 65 is installed between the juxtaposed surfaces of the retainer 59 and the housing 51 to assure a tight seal along the circular edge of the bladder 61 which forms the expansible pressure chamber.

As earlier indicated, the assembled valve has the occluder or occluders oriented in the closed position so that, when the pressure chamber 63 is caused to expand by the injection of fluid under pressure, the bladder 61 will conform to and totally fill the entire interior downstream region of the mechanical valve, applying omnidirectional force thereto. This force will be equally applied to the interior surfaces of the tubular valve body and the downstream surfaces of the occluder or occluders, and a pressure is employed which exceeds normal service loading, i.e. the conditions which will be experienced by an implanted valve. The fluid used may be gas, liquid or any other medium that can be caused to apply omnidirectional force within a confined chamber. The preferred fluid is compressed air, but nitrogen or some other equivalent inert gas may also be employed. Alternatively, liquids such as water or the like may be employed. Moreover, if desired, water or air or nitrogen for example, could be employed without a bladder because the valve design is usually such that the amount of leakage that will occur in the closed position is minimal and will not prevent the build up of pressure to the desired level within the downstream region of the valve being proof tested. On the other hand, a gel-like or other semi-solid material, for example a urethane gel-like substance, might also be used so long as it would retain its integrity and when pressurized, either mechanically by a piston or pneumatically, would apply omnidirectional force within the downstream section of a valve. Therefore, for purposes of this patent application, the loading of such a semi-solid, gel-like material is to be considered within the definition of the application of fluid loading.

As can be seen in FIG. 1, the cap section 23 carries a mounting bracket 69 which is rigidly affixed thereto. The mounting bracket 69 pivots on a shaft 71 carried by a block 73 that is affixed to the stand 17. The bracket carries an upstanding apertured lug 75 which is joined by a pin to a link 77 that is joined by an adjustable connector 79 to a locking toggle mechanism 81 which includes an upstanding handle 83. Manipulation of the handle 83 in a forward direction, as shown in FIG. 1, locks the cap section 23 against the holder section 21 of the fixture 15 so that the proof testing is ready to take place. Following completion of the proof testing, by swinging the handle 83 rearward, the link 77 is caused to move in the right-hand direction causing the cap section to swing into an open orientation where the valve that was proof tested can be withdrawn and replaced by the next heart valve to be tested.

A suitable fluid supply 85 is used that contains controls to allow the operator to set a desired fluid outlet pressure. The supply apparatus may include a gas accumulator or a cylinder of compressed gas suitable to supply fluid at an adequate pressure. Generally, the fluid supply 85 includes by a cylinder of compressed gas, e.g. air, nitrogen, argon, etc., that is equipped with a standard filter to remove any particulate contaminants and a pressure regulator. As shown schematically in FIG. 1, the overall fluid supply system includes a first pressure gauge 87 which reads the pressure in the supply line leading to a metering valve 89. Downstream of the metering valve 89, there is a solenoid-operated, 3-way valve 91 which in the open position allows fluid flowing through the metering valve 89 to reach the line 19 leading to the pressure chamber 63, which line includes a second pressure gauge 93. In one position, the 3-way valve opens the supply line 19 to exhaust, thus reducing the interior of the pressure chamber 63 to atmospheric pressure at the end of a pressure test and allowing the bladder 61 to retract to its unexpanded orientation. In another position, the 3-way valve simply closes both the upstream and downstream fluid supply lines. The 3-way solenoid-controlled valve 91 is electronically connected to the control system 27 which steps the valve to the desired position.

A heart valve such as the On-X valve is assembled by installing the two leaflets in the tubular valve body as described in the '324 patent. A cup 35 of the desired size is installed in the holder section 21 of the fixture 15 while sliding the actuator 39b inward to pivot the first pair of curved levers 45 to radially withdraw the spring-loaded slides. The waveguides 31 have cylindrical sections that are slidably received in the cup prior to its installation, and a separate pair of waveguides are used with each different size cup. By sliding the other thumb actuator 39a inward, the second pair of pivoting levers 44 are caused to simultaneously engage both waveguides causing the cylindrical sections thereof to slide radially outward in the passageways 43 in the sidewall of the cup 35. Such movement sufficiently withdraws the waveguides 31 so that the flared entrance end of the valve will be allowed to pass as it is loaded into the cup.

The assembled valve to be tested is then placed in the removable cup 35 of the proof testing fixture with its flared entrance down so that the downstream end of the mechanical valve faces upward. Once the actuator 39a is released, the spring-loaded slides 47 cause the diametrically opposed waveguides 31 to contact the outer cylindrical surface of the valve body. With the valve in place in the cup 35, and the adaptor ring 41 in place about its downstream end, the handle 83 of the toggle mechanism is swung forward, causing the cap portion 23 of the fixture to pivot downward about the shaft 71 on which the bracket 69 is mounted so that the flexible bladder 61 is now positioned above the interior of the downstream end of the heart valve. The toggle mechanism 81 has an overcenter action which causes the cap section 23 to be locked in place in contact with the holder section 21; the adjustable coupling 79 permits locking to be achieved with only a minimum force between the two fixture sections.

With the proof testing ready to begin, the control system 27 is actuated which causes fluid pressure to build up within the pressure chamber 63 to the desired level; the presence of the metering valve 89 prevents any shock by slowing the pressure rise. The fluid pressure causes the bladder 61 to expand and move into surface contact with the entire interior section of the downstream end of the valve and with the outflow surfaces of the two leaflets which are held in the closed position by gravity. The supply system allows gas flow through the metering valve 89 at a rate such to permit the full desired testing pressure of about 25 psig to be reached during a time period of about 5 seconds, so as to avoid any sudden shock to the valve. Throughout this fluid loading of the downstream section of the valve, the waveguides 31 are in physical contact with the exterior surface of the valve body as a result of the spring-loaded slide arrangement 47, and any acoustic emissions that occur in the assembled valve are transmitted through the waveguides to the associated piezoelectric transducers 29 which are in electrical connection with the panel 27 and its meters that form a part of the control system.

It has been ascertained that pyrolytic carbon, as well as other nonmetallic, crystalline material in which microcrack growth may occur that may potentially lead to failure, generates acoustic emissions when components of such materials are stressed by the application of a mechanical load. More importantly, when as a result of an imperfection in the crystalline structure of the component a microcrack initiates or propagates, transient elastic sound waves of a now-determined character are generated by the rapid release of energy at a localized point within such component. These acoustic emissions, i.e. sound waves generated from such a cracking event, travel in all directions through the component and have a broad band frequency. It has been found that, if any such component is in intimate contact with another component which has similar acoustic impedance, these sound waves will easily travel across such an interface.

In such an assembled heart valve, sound waves generated in one of such leaflets will travel to the annular valve body in which the leaflets are mounted. Waveguides 31 are maintained in contact with the exterior surface of the valve body, and sound waves generated in either a leaflet or in the valve body itself will travel through these waveguides so long as they are in intimate contact with, i.e. coupled with, the exterior surface of the valve body at the interface. In the arrangement used, these sound waves are carried by the waveguides 31 to the sensors which are associated therewith and cause mechanical movement of piezoelectric crystals that are used as the transducers 29, i.e. the sound waves generate stresses in such crystals. Alternatively, the transducers could be directly coupled to the exterior of the valve body or to one of the other interconnected components, but the present arrangement facilitates easier loading of valves being tested.

When a piezoelectric crystal is stressed, it produces a detectable voltage. The control system 27 measures this voltage and analyzes certain features of it, such as amplitude, duration, rise time and acoustic energy in order to characterize the acoustic emissions that are detected during the time period that the assembled valve is being loaded. The test is not one of duration; thus, the period during which the valve is maintained at the full loaded pressure may only be momentary or for a few seconds. Generally, the valve will be exposed to elevated pressure for only about 1–10 seconds, and usually for not more than about 5 seconds, as it is not felt that such exposure to pressure for any longer time is required for adequate proof testing to detect potential microcrack defects. Proof testing of the On-X valve is effectively performed by using a top pressure of about 26 psig and then promptly exhausting the pressure chamber, which is considered to provide an adequate test.

In an example of a proof test of an assembled On-X valve, electrical power is supplied to the control system 27, and it is verified that air is being supplied to the metering valve 89 at a pressure of about 26 psig. Because heart valves vary in size, a plurality of different diameter cups 35 and associated pairs of waveguides 31 are provided to accommodate valve bodies of different exterior diameters. The appropriate cup 35 for the valve being tested is selected and installed, along with its associated waveguides 31, in the holder section 21 of the fixture while sliding the actuator 39*b* inward to pivot the curved levers 45 to withdraw the spring-loaded slides. Wires from the transducers 29 carried by the slides are connected to the control system 27. With the appropriate size cup installed, the lower holder subassembly 21 is ready to receive the assembled heart valve to be tested.

To provide effective coupling at the interface and avoid any potential scratching of the valve body, a thin film of coupling material, as known in this art, is preferably applied at the interface prior to its insertion into the holding cup; the film assures good travel of sound across the interface with the waveguide 31 by minimizing any effect of surface imperfections. Each cup 35 is equipped with a pivoting ejector which is operated by the actuator 39 in order to easily remove the valve without removing the cup from the main body of the fixture. To install the assembled bileaflet valve with its entrance region oriented downward, the actuator 39*a* is pressed radially inward to engage and withdraw the waveguides 31. With the valve in place with its inflow edge resting on a flange at the bottom of the otherwise open cup, the actuator 39*a* is released. The release of the actuator 39*a* releases the curved levers 44 and allows the waveguides to move into physical contact with the surface of the valve body of the assembled bileaflet valve to which the couplant material has been applied, under the bias of the spring-loaded slides 47. A flat adaptor ring 41 is fitted over the downstream end of the valve, which ring 41 has a frusto-conical exterior surface which mates with that at the upper edge of the cup 35. It assures that the valve remains centered in the cup, so that both the waveguides will be in physical contact with diametrically opposed exterior surface regions of the valve body and assures that, when the bladder 61 is expanded, it will fill the interior of the valve. As previously indicated, the handle 83 is then swung to its locked position clamping the two sections of the fixture 15 together.

The control system 27 is then activated to carry out the proof testing steps, and it is conveniently automated by utilizing a simple computer program for each valve design. A state-of-the-art program for a microcomputer of the general type disclosed in the '094 patent could be used, for example, to control the automated testing which will follow the locking of the fixture by swinging forward of the handle on the toggle mechanism 81. Each test for a specific valve design will be dependent upon the acoustic impedance of the material in question and to a lesser degree the shape of the valve itself. Such factors may influence how effectively waveguides can be maintained in physical contact with the valve. A number of factors will have an effect upon what magnitude of signals from the piezoelectric crystals that will be considered to be acceptable, and above which limits, such signals will require rejection on the basis of likelihood of potential crack initiation and/or propagation.

Very generally, acoustic impedance is a function of the elastic modulus of the material divided by the density of the material, and the greater the acoustic impedance, the greater is the attenuation of sound within a particular crystalline material. Moreover, each type of piezoelectric crystal has a resonant frequency, as a result of which, when two different types of piezoelectric crystals are used to detect sound from the same source, the signals which they produce will have different acoustic characteristics. Attenuation also occurs at the area of contact between the sensor and the source component, which in this instance would be the interface between the waveguide 31 and the exterior of the valve body; generally, the greater the contact area, the less will be the attenuation. Waveguides are frequently used to allow acoustic communication between a source and a sensor when the environment or the available space might not otherwise facilitate direct sensor-to-component coupling. Of course, a waveguide may also alter the characteristic of the detected signal due to any acoustic impedance mismatch, to the amount of contact area between the waveguide and the source, and to the shape and the material properties of the waveguide itself, and such is taken into consideration.

It can be seen from the foregoing that, because of the number of variables, proof testing should be properly validated for each particular test apparatus that is designed in order to determine what signals from transducers will be indicative that crack propagation and/or initiation has occurred while the assembled prosthetic heart valve is being fluid loaded. Practically, this can only be done by actual testing of valves of a particular nonmetallic, crystalline material in their assembled condition, particularly when a fixture is employed that includes the use of waveguides or other means to facilitate transmission of sound ultimately to a transducer that is selected for monitoring such sounds. Usually monitoring is designed to detect sound having a broadband wave length between about 10 kHz and about 1 mHz; however, it may be acceptable to monitor in a narrower range from about 80 kHz to about 800 kHz, or even from about 200 to about 800 kHz.

Depending upon the material from which the component being tested is made, either a single parameter or a combination of parameters will be selected that will be appropriately indicative of whether or not there was an occurrence of crack initiation and/or propagation during fluid loading. As an example, duration of the electric voltage signal that is monitored might be used as the pass-fail criterion. For example, in testing the On-X valve, the acoustic emission detection system is set to monitor both for amplitude of signals received and for relative energy of signals received. Relative energy is a measure of signal strength which is calculated by integrating the area under a curve based upon the amplitude and duration of the signal. As an example, for proof testing the On-X valve which includes three pyrocarbon coated graphite components, i.e. two leaflets and a generally tubular valve body, which are positioned for testing in a fixture which includes a pair of spring-loaded diametrically opposed waveguides in association with piezoelectric sensors, it is determined empirically, for this particular valve assembly and fixture, that detection of a voltage signal whose amplitude feature exceeds an amplitude of about 70 acoustic emission decibels (dB AE) or whose energy feature exceeds an energy level of about 40 AE energy units will constitute a failure of the proof test as constituting detection of an acoustic emission very likely to be indicative of microcrack initiation and/or propagation. Dependent upon the level of record-keeping felt desirable, the AEDS 13 can include a printer that will, upon actuation, provide a printout of the characteristics of the signals monitored during each proof testing, which can then become part of the fabrication history of each particular prosthetic heart valve.

As earlier indicated, the proof testing procedure can be automated so that, once the control system 27 is activated, gas will be slowly fed through the metering valve 89 into the pressure chamber 63 until the gas pressure in the supply line 19 reaches the desired value of about 26 psig, while recording any electric signals generated by the transducers as a result of acoustic emissions from any of the three pyrocarbon-coated components. Once the desired pressure has been reached in the pressure chamber 63, as indicated by the second pressure gauge 93, the system will shortly thereafter cause the 3-way valve to vent the line downstream therefrom to exhaust so that the bladder 61 returns to its at rest orientation and then signaling completion of the test when the line 19 reaches 0 psig. A printed report may be automatically generated or the operator can ask for such a report if it has been observed that the assembled valve has passed the proof test. The latter alternative would allow the printing of a report to be bypassed in an instance where it was observed that voltage signals of such a magnitude were detected that the assembled valve being tested would have failed this quality control test.

The fixture 15 is then opened by swinging the handle 83 of the toggle mechanism back to pivot the cap section 23 out of the way and expose the upper end of the holding fixture. Thereafter, actuation of the valve ejector 39a first withdraws the waveguides by sliding them radially outward and then through further travels engages the pivoting ejector that lifts the valve that was just tested and facilitates removal of the assembled valve and the centering ring 41 from the cup. Thereafter, the plastic wrap would be removed from the outer surface of the valve, and the assembled valve would be placed in a processing record bag and associated with the printed report which reflects the successful completion of the proof test.

Although the invention has been described with regard to certain preferred embodiments which constitute the best mode presently known, it should be understood that various changes and modifications as would be obvious to those having ordinary skill in this art may be made without departing from the scope of the invention set forth in the claims appended hereto. As previously indicated, it should be understood that the pass-fail criteria for a proof test such as this for monitoring acoustic emissions will of necessity vary not only because of the characteristics of the one or more components of the assembled prosthetic valve that is being tested but also because of the inherent character of the physical arrangement and materials of the fixture and the transducers themselves. Accordingly, although operations to date have validated the proof testing method and apparatus hereinbefore described as being appropriate for quality control of mechanical heart valves of this general type, it should be clear that the pass-fail criteria in each such instance should be individually determined.

The disclosures of all of the U.S. patents mentioned hereinbefore are expressly incorporated herein by reference.

Particular features of the invention are emphasized in the claims which follow.

What is claimed is:

1. A method of proof testing an assembled mechanical heart valve prosthesis having a valve body and at least one movable occluder, at least one of which has a pyrocarbon surface in which micro crack growth may occur, which method comprises:

subjecting the assembled valve prosthesis to loading, with the at least one occluder in the closed position, so as to exceed normal service loading on a downstream side of the occluder, acoustically monitoring the valve prosthesis during such loading to detect sounds by measuring transduced voltage signals for such signals whose energy feature exceeds a predetermined acoustic energy level so as to be indicative of crack nucleation and/or incremental crack extension, and rejecting a valve prosthesis where such sounds are detected.

2. The method according to claim 1 wherein said loading is by fluid-loading so as to create omnidirectional pressure within a downstream region of the valve body.

3. The method according to claim 2 wherein said fluid-loading creates a pressure of at least about 10 psig therewithin.

4. The method according to claim 2 wherein said fluid-loading is carried out by pneumatically pressurizing a flexible bladder.

5. The method according to claim 4 wherein said fluid-loading is carried out by raising the pressure within said bladder from atmospheric pressure to at least about 25 psig over a time period of at least about 4 seconds.

6. The method according to claim 1 wherein said monitoring includes coupling a waveguide with an exterior surface of said valve body, said waveguide being adapted to conduct sound having a broadband wavelength between about 10 kiloHertz and about 1 megaHertz to an associated piezoelectric sensor.

7. The method according to claim 6 wherein said coupling step includes inserting a couplant material between said exterior surface of said valve body and a juxtaposed surface of said waveguide.

8. The method according to claim 6 wherein acoustic emissions from the assembled valve prosthesis are monitored for voltage signals from said piezoelectric sensor whose amplitude feature exceeds a predetermined amplitude.

9. A method of proof testing an assembled mechanical heart valve prosthesis having a pyrocarbon valve body and at least one pyrocarbon movable occluder, which method comprises:

sudjecting the assembled valve prosthesis to fluid-loading with the at least one occluder in the closed position so as to create omnidirectional pressure of at least about 10 psig therewithin on a downstream side of the occluder, acoustically monitoring the valve prosthesis during such fluid-loading by directly or indirectly coupling the valve body with a transducer that includes a piezoelectric element so as to detect broadband wavelength sounds, and rejecting a valve prosthesis where sounds are detected in the form of voltage signals whose amplitude feature exceeds a predetermined amplitude that is indicative of crack nucleation and/or incremental crack extension in pyrocarbon.

10. Apparatus for proof testing an assembled mechanical heart valve prosthesis having a valve body and at least one movable occluder, at least one of which assembled components has a surface that is formed of a material in which microcrack growth may occur, which apparatus comprises:

a fixture for holding the valve body of the assembled valve prosthesis with the at least one movable occluder in the closed position, acoustic sensing means which includes a waveguide and transducer means that are adapted to detect sound emitted from said assembled components and generate a responsive electrical signal, spring-biasing means connected to said waveguide which causes said waveguide to seat in close contact with an exterior surface of the valve body being tested, means for fluid-loading an interior region of said assembled valve prosthesis at a location downstream of said closed occluder so as to apply omnidirectional pressure therewithin of at least about 10 psig, and means for monitoring output signals from said transducer means during fluid-loading of said interior region of the valve prosthesis to detect signals resulting from sounds being emitted that are indicative of crack nucleation and/or incremental crack extension in the assembled valve prosthesis.

11. The apparatus according to claim 10 wherein said fluid-loading means includes a flexible, extensible bladder and means for pneumatically pressurizing said flexible bladder.

12. The apparatus according to claim 11 wherein said fluid-loading means further includes means for raising said pneumatic pressure within said flexible bladder in a programmed manner over time.

13. The apparatus according to claim 10 wherein said transducer means includes a piezoelectric element.

14. The apparatus according to claim 13 wherein said monitoring means includes means for measuring voltage signals generated by said transducer means.

15. The apparatus according to claim 14 wherein said monitoring means includes means for measuring voltage signals corresponding to the energy generated by acoustic emissions from the assembled valve prosthesis.

16. The apparatus according to claim 10 which includes a plurality of interchangeable cups, wherein said fixture is adapted to receive said interchangeable cups which are sized to support valves having generally tubular pyrolytic carbon valve bodies with exterior diameters of different sizes in an orientation for proof testing and wherein said fluid-loading means is adapted to provide omnidirectional pressure within the interior region of the valve body of at least about 25 psig while the valve body is supported in one of said interchangeable cups.

17. The apparatus according to claim 16 wherein said fixture includes means for ejecting said generally tubular valve body from said one of said interchangeable cups in an axial direction.

18. The method according to claim 9 wherein said acoustically monitoring is carried out for sound having a wavelength between about 80 kHz and about 800 kHz.

19. The method according to claim 18 wherein said monitoring is carried out so as to detect any voltage signal having an amplitude exceeding about 70 acoustic emission decibels and rejecting a valve prosthesis where a voltage signal having at least such amplitude is detected.

20. The apparatus according to claim 13 wherein a pair of diametrically opposed waveguides are provided which are spring-biased to contact diametrically opposite regions of the exterior surface of a tubular valve body.

* * * * *

UNITED STATES PATENT AND TRADEMARK OFFICE
CERTIFICATE OF CORRECTION

PATENT NO. : 6,062,075
DATED : May 30, 2000
INVENTOR(S) : Ritz et al.

It is certified that error appears in the above-indentified patent and that said Letters Patent is hereby corrected as shown below:

IN THE CLAIMS:

Column 12, line 61 (claim 5), "4" should read --5--.

Signed and Sealed this

Twenty-seventh Day of March, 2001

*Attest:*

NICHOLAS P. GODICI

*Attesting Officer*     *Acting Director of the United States Patent and Trademark Office*